US010172785B2

(12) United States Patent
Leplanquais et al.

(10) Patent No.: US 10,172,785 B2
(45) Date of Patent: Jan. 8, 2019

(54) *DENDROBIUM CHRYSOTOXUM* EXTRACT AND ITS COSMETIC USE AS AN ANTI-AGING AGENT

(71) Applicant: LVMH RECHERCHE, Saint Jean de Braye (FR)

(72) Inventors: Virginie Leplanquais, Donnery (FR); Patrice Andre, Neuville Aux Bois (FR); Virginie Pecher, La Chapelle Saint Martin (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 628 days.

(21) Appl. No.: 14/836,322

(22) Filed: Aug. 26, 2015

(65) Prior Publication Data

US 2015/0359733 A1 Dec. 17, 2015

Related U.S. Application Data

(62) Division of application No. 13/231,466, filed on Sep. 13, 2011, now abandoned.

(30) Foreign Application Priority Data

Sep. 14, 2010 (FR) ...................... 10 57336

(51) Int. Cl.
| | | |
|---|---|---|
| *A61K 8/97* | (2017.01) | |
| *A61K 36/53* | (2006.01) | |
| *A61K 36/8964* | (2006.01) | |
| *A61K 36/8984* | (2006.01) | |
| *A61Q 19/08* | (2006.01) | |
| *A61K 8/99* | (2017.01) | |
| *A61Q 19/00* | (2006.01) | |
| *A61Q 19/04* | (2006.01) | |
| *A61Q 19/06* | (2006.01) | |

(52) U.S. Cl.
CPC ................ *A61K 8/97* (2013.01); *A61K 8/975* (2013.01); *A61K 8/99* (2013.01); *A61K 36/53* (2013.01); *A61K 36/8964* (2013.01); *A61K 36/8984* (2013.01); *A61Q 19/00* (2013.01); *A61Q 19/007* (2013.01); *A61Q 19/04* (2013.01); *A61Q 19/06* (2013.01); *A61Q 19/08* (2013.01); *A61K 2236/333* (2013.01); *A61K 2800/43* (2013.01); *A61K 2800/5922* (2013.01); *A61K 2800/782* (2013.01); *A61K 2800/80* (2013.01)

(58) Field of Classification Search
None
See application file for complete search history.

(56) References Cited

U.S. PATENT DOCUMENTS

2004/0028643 A1 2/2004 Chiba et al.

OTHER PUBLICATIONS

"Medicinally used Dendrobium species—Dendrobium chrysotoxum—Gold Orchid", Nature Products., Network (Apr. 3, 2009), 16 pages, XP002633741, Internet: URL: http://replay.waybackmachine. Org/20090403190953/http.
Chen et al., "1,4,5-Trihydroxy-7-methoxy-9 H-fluoren-9-one, a new cytotoxic compound from Dendrobium chrysotoxum", Food Chemistry vol. 108 No. 3, 14, (Dec. 14, 2007), pp. 973-976, XP022461504.
Jin et al., "Dendroflorin retards the senescence of MRC-5 cells", Pharmazie , vol. 63, (Apr. 2008), pp. 321-323.
Gutierrez "Orchids: A review of uses in traditional medicine, its phytochemistry and pharmacology", Journal of Medicinal Plants Research, vol. 4(8), (Apr. 18, 2010) pp. 592-638.
Yang et al., "Simultaneous determination of phenols (bibenzyl, phenanthrene, and fluorenone) in Dendrobium species by high-performance liquid chromatography with diode array detection", Journal of Chromatography A, 1104, (2006) pp. 230-237.
Leplanquais, "Mesure de lactivite anti-age delextrait de Dendrobium chrysothoxim", LVMH Recherche Parfums & Cosmetiques, (May 7, 2010), pp. 1-7.
Deveraux et al. "IAP Family Proteins-Suppressors of Apoptosis", Genes & Development, No. 13, (1999), pp. 239-252.
Dallaglio et al., "Endogenous Survivin Modulates Survival and Proliferation in UVB-Treated Human Keratinocytes", Experimental Dermatology No. 18, Oct. 27, 2008, pp. 464-471.
Zhang et al. "TRAF3 Interacts With SMAC/Diablo and Enhances the Proapoptotic Effect of SMAC/Diablo in Cytoplasm", Biochimica et Biophysica Sinica, (2007), 39(2), pp. 108-116.
Kurita-Ochai et al., "Butyric Acid Induces Apoptosis Via Oxidative Stress in Jurkat T-Cells", Research Reports, J Dent Res. 89 (7), (2010), pp. 689-694.
Aziz et al. "Prevention of Ultraviolet-B Radiation Damage by Resveratrol in Mouse Skin Is Mediated Via Modulation in Survivin", Photochemistry and Photobiology, (2005) No. 81, pp. 25-31.
Ng et al. "Antioxidative Activity of Natural Products From Plants", Life Sciences, vol. 66, No. 8, Sep. 24, 1999, pp. 709-723.
"Can we prevent aging"; Retrieved from the Internet on: Nov. 16, 2012, Retrieved from <URL: http://www.nia.nih.gov/health/publication/can-we-prevent-aging>.

(Continued)

*Primary Examiner* — Terry A McKelvey
*Assistant Examiner* — Catheryne Chen
(74) *Attorney, Agent, or Firm* — Hamre, Schumann, Mueller & Larson, P.C.

(57) ABSTRACT

The invention relates to a cosmetic composition comprising at least one extract from the orchid *Dendrobium chrysotoxum* as an active agent and at least one cosmetically acceptable excipient.

Figure 1:
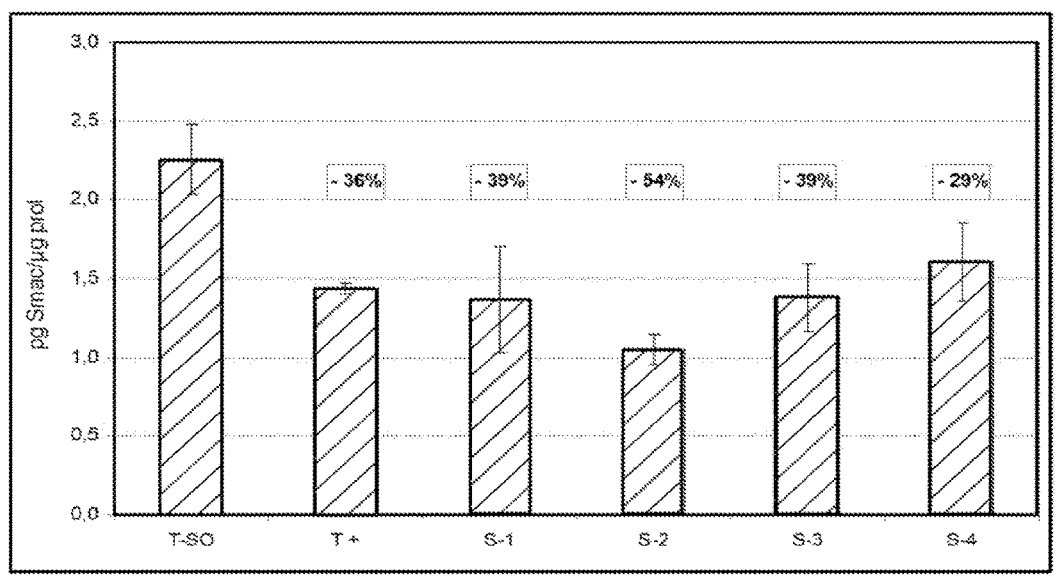

The invention relates to the use in a cosmetic composition of an extract from the orchid *Dendrobium chrysotoxum* as an active agent for preventing or delaying the appearance of the signs of skin ageing or for slowing or attenuating the effects thereof, or else also for promoting cell or tissue longevity.

The invention in particular relates to an orchid extract inhibiting the expression and/or the activity of the mitochondrial protein Smac/DIABLO.

11 Claims, 1 Drawing Sheet

(56) References Cited

OTHER PUBLICATIONS

Stibich, Mark: "Free Redical Theory of Aging"; Web Update date: Aug. 14, 2014, Retrieved from the Internet on: Mar. 21, 2015], Retrieved from <URL: http://longevity.about.com/od/researchandmedicine/p/age_radicals.htm?p=1>.
Brannon, H: Retrieved from the Internet on: Dec. 3, 2012, Retrieved from <URL: http://dermatology.about.com/cs/beauty/a/suneffect.htm?p=1>.
Sastre et al. :The Role of Mitochondrial Oxidative Stress in Aging, 2003, Free Radic Biol Med, 35:1-8.
(U1) forskolin 2005; http://web.archive.org/web/20051024120013/http://www.advance-health.com/coleus.html.

DENDROBIUM CHRYSOTOXUM EXTRACT AND ITS COSMETIC USE AS AN ANTI-AGING AGENT

The invention relates to a novel cosmetic composition, comprising at least one extract from the orchid *Dendrobium chrysotoxum* as an active agent and at least one cosmetically acceptable excipient, in particular for preventing or delaying the appearance of the signs of skin ageing, for slowing or attenuating the effects thereof, or else also for promoting cell or tissue longevity.

STATE OF THE ART

Skin ageing reveals itself in numerous changes intrinsic to the skin and the progressive appearance of visible signs which modify the beauty and the quality of the skin. The skin texture is less fine, and numerous skin blemishes develop.

At the cellular level, the ageing results in a progressive deterioration in biological mechanisms such as the slowing of the synthesis of structural proteins (collagen, elastin).

Apoptosis, a type of programmed cell death, is an active biological process of elimination of cells from the body, by fragmentation and under genetic control.

The elimination can be natural (surplus cells in a tissue or induced by various stresses.

The biological cascade of apoptosis is known and brings into play a number of effectors such as proteases of the caspase family.

Inhibitors of apoptosis (IAP) are known, having the function of blocking the activation of pro-caspases and inhibiting the activity of mature caspases, which results in slowing of the phenomenon of apoptosis (Deveraux et al, *Genes Dev.* 13 (1999), pp. 239-252).

Among the IAP, mention is made of survivin, a bifunctional protein, capable of simultaneously controlling the apoptosis of cells and of regulating their cell cycle.

Survivin is a regulator of the survival and the resistance of the keratinocytes to the stresses that can induce this apoptosis phenomenon. It also regulates their capability for renewal and regeneration of the epidermis. It thus makes it possible to save the cellular capital of the epidermis and to maintain effective cell renewal (Dallaglio, et al., *Experimental Dermatology*, 18 (5) 464-72).

The production of survivin is tightly controlled by the mitochondrial protein Smac/DIABLO (Second Mitochondrial Activator of Caspases or Direct IAP Binding Protein with Low pI), liberated during apoptosis.

This protein, Smac/DIABLO, synthesized in the form of a 29 kDa precursor, is translocated in the mitochondrion by its N-terminal domain which possesses a mitochondrial location signal. This precursor is then cleaved to give rise to a 23 kDa mature protein (Zhang et al, *Acta Biochim. Biophys. Sin.* 2007, 39 (2), 108-116).

It is known that UV radiation or free radicals such as the ROS induce cell stress in the skin, a stress which is involved in skin ageing.

In response to stimuli such as UV radiation or reactive oxygen species (ROS), the mature mitochondrial protein Smac/DIABLO is released into the cell cytosol where it acts as an inhibitor of the IAP. In the form of dimers, it binds to the IAP and thus blocks the inactivation of the caspases (Kurita-Ochiai T. et al, *J. Dent. Res.* 2010, 89(7), 689-694).

Similarly, in response to these same stimuli, reduced production of Smac/DIABLO has been demonstrated, comitantly with overexpression of survivin which increases cell longevity (Aziz M H. et al, *Photochem. Photobiol.* 2005, 81(1), 25-31).

It is thus of particular interest, in order to combat skin ageing more effectively, to be able to have available in cosmetics one or more other active agents capable of significantly reducing the expression and/or the activity of this protein Smac/DIABLO in the cells of the epidermis and to allow the IAP to inhibit the caspases in such a way as to improve cell reactivity towards the stress induced by UV radiation or free radicals and to promote cell longevity.

However, until now, such agents for cosmetic applications have never been described.

It is thus particularly surprising to have demonstrated that an orchid extract exhibits such an inhibitory effect on the expression of the protein smac/DIABLO, and more particularly an extract of flowers of the orchid *Dendrobium chrysotoxum*.

Among the orchids, several species belonging to the genus *Dendrobium* are known in traditional Chinese medicine. However, it is the extracts of stems or leaves which are used (Gutierrez R M P, *J. Med. Plant Res.*, 2010, 4 (8), 592-638).

In particular, erianin has been isolated from an extract of stems of *Dendrobium chrysotoxum* (N G et al, *Life Science*, 2000, 66 (8), 709-23), a compound for which an antioxidant activity has been demonstrated in the rat.

Until now, no particular activity has ever been demonstrated for an extract of flowers of *Dendrobium chrysotoxum*.

PURPOSES OF THE INVENTION

The principal purpose of the invention is to provide novel cosmetic compositions, intended in particular to prevent or delay the appearance of the signs of skin ageing, or to slow or attenuate the effects thereof, or else also to promote cell or tissue longevity, this activity being obtained in particular by inhibition of the expression and/or the activity of mitochondrial protein Smac/DIABLO.

It is also a purpose of the invention to provide a cosmetic care method using said cosmetic compositions.

It is also a purpose of the invention to provide a novel extract of plant origin reducing the expression and/or the activity of the mitochondrial protein Smac/DIABLO, in the skin and in particular in the epidermis.

Finally, it is a purpose of the invention to solve the totality of the technical problems by a simple, relatively low cost solution, usable on the industrial scale, in particular in the cosmetics industry.

SUMMARY OF THE INVENTION

The inventors of the present invention have now demonstrated that the treatment of normal human keratinocytes (NHK) with at least one extract of an orchid of the species *Dendrobium chrysotoxum*, induces a significant decrease in the expression and/or the activity of the mitochondrial protein Smac/DIABLO.

This effect of inhibition of the expression and/or the activity of said protein results in a more intense activity of limitation of apoptosis of the cells and regulation of their cell cycle by the IAPs.

Thus, according to a first aspect, the invention relates to a cosmetic composition comprising said extract and to a cosmetic or dermatologic care method characterized in that it comprises the application of an effective quantity of a composition according to the invention onto the part of the skin of the face or the body concerned.

According to a second aspect, the invention relates to an orchid extract, in particular of the species *Dendrobium chrysotoxum*, for preventing or delaying the appearance of the signs of skin ageing, or slowing or attenuating the effects thereof, or else also promoting cell or tissue longevity, in particular in that it inhibits the expression and/or the activity of the mitochondrial protein Smac/DIABLO (extract of the invention), and its use as an active agent in cosmetic or dermatologic compositions

DESCRIPTION OF THE INVENTION

A first subject of the invention relates to a cosmetic composition, comprising at least one extract of flowers of the orchid *Dendrobium chrysotoxum* as an active agent and at least one cosmetically acceptable excipient.

The cosmetic composition is more particularly intended to prevent or delay the appearance of the signs of skin ageing or to slow or attenuate the effects thereof, or else also to promote cell or tissue longevity.

The extract of the invention advantageously inhibits the expression and/or the activity of the mitochondrial protein Smac/DIABLO.

The plant material preferably consists only of flowers of the orchid *Dendrobium chrysotoxum*. However, the invention also relates to combinations of the extract of the invention with any extract of another part of the orchid *Dendrobium chrysotoxum*, preferably prepared under the same conditions as the extract of the invention, or compound isolated from one of these extracts.

The extract of the invention can be prepared by different extraction processes known to those skilled in the art.

Advantageously the extract is obtained by means of a polar solvent or a mixture of polar solvents.

As the polar solvent, a solvent or a mixture of solvents is advantageously selected from water, a $C_1$-$C_4$ alcohol, for example ethanol, a $C_2$-$C_6$ glycol, preferably selected from glycerol, butylene glycol and propylene glycol, or else also any mixture thereof.

According to a preferred embodiment, the $C_1$-$C_4$ alcohol is ethanol.

In particular, the plant material is extracted by means of a solvent comprising at least 50% v/v of ethanol and up to 100% v/v of ethanol, the balance if necessary consisting of another polar solvent and in particular of water.

The extraction can be performed hot under reflux or else at ambient temperature.

According to a preferred modification of the invention, the extraction is effected by maceration of the plant material in a polar solvent or a mixture of polar solvents such as aforesaid, at ambient temperature for several hours.

According to one modification, the extract is a dry extract, possibly brought into solution.

Prior to the extraction step itself, the plant material may have been dried and/or ground and/or delipidated.

The delipidation of the extract can be effected by means of nonpolar solvents, such as for example a $C_6$-$C_7$ alkane, or else also by $CO_2$ in the supercritical state, possibly with the addition of a polar co-solvent such as ethanol, methanol or else caprylic/capric triglycerides (Mygliol 812®, Hüls AG).

The extraction can also, optionally, comprise at least one supplementary stage of decolourization or purification of the extract of the invention.

The decolourization of the extract can for example consist in a treatment of said extract with a nonpolar solvent of the type of those used to delipidate the extract.

The extraction can be completed by a stage of partial or total removal of the extraction solvents.

In the first case, the extract is generally concentrated until an aqueous concentrate not containing a significant quantity of organic solvents is obtained, and in the second case a dry residue is obtained.

Alternatively, the product from the extraction stage can be lyophilized or atomized to take the form of a powder.

As an active agent in the cosmetic composition according to the invention, the extract is used in the dry state or else in solution or suspension in a solvent or a mixture of cosmetically acceptable solvents, which can be identical or different from that or those used for the extraction.

The cosmetic composition comprises an effective quantity of extract for obtaining the desired effect, in particular an inhibition of the expression and/or of the activity of the mitochondrial protein Smac/DIABLO.

The composition thus preferably comprises from 0.0001% to 1% by weight of dry extract, preferably from 0.001% to 0.01% by weight relative to the total weight of the composition.

The properties of the extract of the invention can also be obtained or improved in cosmetic compositions wherein the extract of the invention is combined with other cosmetically acceptable active agents, in the form of purified substances and/or extracts, in particular plant extracts, exhibiting cosmetic effects similar and/or complementary to those of said extract of the invention.

The composition can thus comprise one or more other extracts of plants, and advantageously comprise at least one extract of another part of the orchid *Dendrobium chrysotoxum* or of another orchid or a substance purified from such an extract.

The cosmetic composition can also advantageously comprise one or more other active agents among those which stimulate the expression of survivin such as forskolin or an extract containing these, in particular an extract of *Coleus forskolii*, or else also a plant extract obtained from a plant species selected from *Nostoc commune, Butea frondosa, Neochloris oleabundans, Scenedesmus dimorphus, Curcuma longa, Crocus sativus, Daniellia oliveri, Lepechinia caulescens, Limnophila conferta*, and any mixture thereof.

Finally, the cosmetic composition can comprise other cosmetically acceptable active agents selected from the group of substances having an anti-ageing activity, substances having a depigmenting, whitening or clearing activity on the skin, substances having a slimming activity, substances having a hydrating activity, substances having a calming, soothing or relaxing activity, substances having an activity stimulating the skin microcirculation to improve the lustre of the complexion, in particular of the face, substances having a sebo-regulatory activity for the care of oily skins, substances intended to clean or purify the skin, substances having an anti-radical activity, and any mixture thereof.

Advantageously, the composition of the invention comprises at least one cosmetically acceptable excipient which may be selected from pigments, colorants, polymers, surface-active agents, viscosity agents, perfumes, electrolytes, pH adjusters, anti-oxidant agents, preservatives, and any mixture thereof.

The cosmetic composition can for example be a serum, a lotion, a cream, a hydrogel, preferably a mask, an oil-in-water emulsion, an anhydrous composition, or else be in the form of a stick, a patch, or in the form of a make-up product of the lipstick, mascara or foundation type.

The extract and the composition of the invention exhibit a particularly desired effect for preventing or delaying the appearance of the signs of skin ageing or for slowing or attenuating the effects thereof, or else also for promoting cell or tissue longevity.

A second subject of the invention thus relates to the use in a cosmetic composition of at least one extract of flowers of the orchid *Dendrobium chrysotoxum* as an active agent intended to prevent or delay the appearance of the signs of skin ageing or to slow or attenuate the effects thereof, or else also to promote cell or tissue longevity.

Advantageously, the extract or the composition is as defined above or below.

Advantageously, the composition comprising said extract is itself intended to prevent or delay the appearance of the signs of skin ageing or to slow or attenuate the effects thereof, or else also to promote cell or tissue longevity.

A third subject of the invention relates to a cosmetic care method, in particular for preventing or delaying the appearance of the signs of skin ageing or for slowing or attenuating the effects thereof, or else also for promoting cell or tissue longevity, characterized in that it comprises the application of an effective quantity of a cosmetic composition as defined above onto at least one part of the skin of the face or the body.

Advantageously, the cosmetic composition is applied onto a skin zone of the body or the face exhibiting visible signs of ageing such as the presence of wrinkles or small wrinkles or a loss of lustre of the skin complexion, or other signs such as a loss of elasticity and/or suppleness of the skin, a decrease in the thickness of the skin, and/or an increase in skin dryness or roughness.

The invention also relates to the use of an effective amount of at least one extract of flowers of the orchid *Dendrobium chrysotoxum*, for the preparation of a composition for preventing or delaying the appearance of the signs of intrinsic and/or extrinsic ageing of the skin, or for slowing down the effects thereof. The composition can be especially applied via topical application to at least one area of skin of an individual exhibiting visible signs of ageing such as the presence of wrinkles or small wrinkles or a loss of lustre of the skin complexion, or other signs such as a loss of elasticity and/or suppleness of the skin, a decrease in the thickness of the skin, and/or an increase in skin dryness or roughness. The composition is especially intended to be applied on the skin of an individual being over 35 years old, over 40 years old, over 45 years old, over 50 years old, over 55 years old or even over 60 years old. The composition can advantageously be applied on mature skins. It can be specifically intended to prevent or delay the appearance of the signs of ageing of the skin of the face and/or of the eyes.

A fourth subject of the invention relates to an orchid extract, in particular of the species *Dendrobium chrysotoxum*, inhibiting the expression and/or the activity of the mitochondrial protein Smac/DIABLO.

The extract is advantageously an extract of flowers of *Dendrobium chrysotoxum* as defined above.

The extract is moreover advantageously obtained by means of a polar solvent or a mixture of polar solvents as described above.

Preferably, said extract is a dry extract, possibly brought into solution.

Other purposes, characteristics and advantages of the invention will appear clearly in the light of the explanatory description which follows, made with reference to examples of extract preparation and tests demonstrating the properties of the extract and to examples of a cosmetic composition using such an extract, which are given by way of illustration of the invention without however limiting the scope thereof.

In the examples, all the percentages are given by weight, the temperature is in degrees Celsius and the pressure is atmospheric pressure, unless otherwise indicated.

DESCRIPTION OF DIAGRAMS

FIG. 1 represents the level of expression of the mitochondrial protein Smac/DIABLO (expressed in pg/µg total proteins), measured by an immuno-enzymatic method, after treatment of normal human keratinocytes (NHK) with one of the extracts prepared in Example 1 (S-1 to S-4) and compared with a solvent control (T-SO) and a positive control (T+). The percentages indicated correspond to the percentages inhibition relative to the solvent control (T-SO).

EXAMPLES

Example 1: Preparation of Extracts of Flowers of *Dendrobium chrysotoxum*

Preparation of the Extracts of the Invention

Four extracts as well as two other extracts serving as a comparison were prepared according to the invention.

The plant material of extracts S-1, S-2, S-3 and S-4 consisted of flowers of the orchid *Dendrobium chrysotoxum*. The extracts R and G were obtained from roots of the *Dendrobium chrysotoxum* orchid or from the leaves of the *Grammatophyllum* sp. orchid.

The plant material, in a dry state and ground, was subjected to an aqueous alcohol extraction with 90/10 v/v ethanol/water under reflux for 30 minutes in order to prepare extracts S-1, R and G. The extraction solvent was then removed to obtain a dry extract.

The above extraction was reproduced to obtain the extracts S-2, S-3 and S-4 changing the extraction solvent and the temperature conditions. Two extraction temperatures were tested: ambient temperature (AT) for 16 hours, or else hot (solvent reflux) for at least 30 minutes.

The extracts prepared and their associated extraction yield expressed as percentage (weight/weight) of dry extract relative to the starting plant material in the dry state and ground are summarized below.

| Extract code | Type of extraction | Extraction yield |
|---|---|---|
| S-1 | Ethanol/water 90/10 v/v - reflux | 23.1% |
| S-2 | Ethanol 100% - reflux | 17.0% |
| S-3 | Ethanol/water 70/30 v/v - AT | 27.9% |
| S-4 | Ethanol/water 50/50 v/v - AT | 28.4% |
| R | Ethanol/water 90/10 v/v - reflux | 14.7% |
| G | Ethanol/water 90/10 v/v - reflux | 14.1% |

For the cosmetic activity tests of Example 2 below, a stock solution was prepared for each extract, in which the dry extract was dissolved in DMSO at the concentration of 12.5 mg of extract per mL of solvent.

Example 2: Immunoenzymatic Assay of the Level of Expression of the Protein Smac/DIABLO in Normal Human Keratinocytes (NHK)

2.1—Preparation of the Positive Control and Solutions of Extracts

Forskolin is a known activator of the expression of survivin (cf. example 1 of the patent application FR2932086).

For the test below, an extract of *Coleus forskolii* which contains at the minimum 98% by weight of forskolin was used as the positive control. Such an extract is marketed in the form of powder for example by SIGMA.

The extract powder was dissolved in DMSO so as to obtain a forskolin concentration (molar mass=410.5) of about $10^{-6}$ M.

The solution of the positive control thus prepared was added to the culture medium so as to obtain a dilution to one thousandth, i.e. a forskolin concentration equal to about $10^{-9}$ M.

In parallel, a solvent control (DMSO), diluted to one thousandth in the culture medium, was prepared.

The stock solution of each extract tested (S-1 to S-4, R and G) was diluted in the keratinocyte culture medium in order to obtain a final concentration of extract of 12.5 µg/mL.

2.2—Treatment of the NHK

The cultured NHK were inoculated into 48-well microplates in an amount of 50,000 cells per well, in complete serum-free culture medium (KSFMc, Gibco).

This first culturing day corresponds to D0.

The treatment stage started on D1, after 24 hours of incubation (37° C., 5% $CO_2$) of the NHK.

After removal of the culture medium, this was replaced by new KSFMc medium containing either the extract to be tested or the positive control or else the solvent control (T-SO). Each treatment was effected in triplicate.

After 16 hours of treatment, a period corresponding to the expression peak of survivin in the course of the cell cycle, the NHK were lysed on a half plate in order to perform the assays (lysis buffer prepared extemporaneously according to the protocol described in the Smac/DIABLO protein assay kit (ref. below). The other half plate was rinsed with PBS and then stored at −20° C. in order to assay the total proteins therein by a colorimetric test according to the BCA method (BC Assay Kit, Uptima Interchim) by absorbance measurement at 570 nm.

2.3 Assay Method

The level of Smac/DIABLO produced by the keratinocytes was evaluated with the Duoset Smac/DIABLO ELISA kit (R&D Systems).

The addition of a streptavidin coupled to a chromophore, here HRP (horseradish peroxidase), made it possible to evaluate the enzymatic activity of the latter by addition of its substrate (tetramethylbenzidine) in the presence of hydrogen peroxide.

Once the enzymatic reaction was blocked with sulphuric acid, the presence of Smac/DIABLO was revealed via the colorimetric reaction, proportional to its concentration.

The absorbance was measurable at a wavelength of 450 nm.

A standard range was created on the basis of dilutions of a standard stock solution of Smac/DIABLO, provided in the kit.

2.4—Results of the Assay of the Smac/DIABLO Protein in NHK Lysates

The results are shown in FIG. 1. They are expressed in pg of Smac/DIABLO protein per µg of total proteins (pg/µg prot.).

The percentages inhibition of the production of this protein were calculated relative to the basal level without treatment (TSO). The positive control is forskolin (FSK).

Conclusion

Each of the four extracts of the invention tested exhibited significant activity (S-1: −39%; S-2: −54%; S-3: −39%; S-4: −29%) in reducing the expression of the mitochondrial protein Smac/DIABLO in the NHK, with an efficiency which can be greater than that of the positive control.

By contrast, the root extract of *Dendrobium chrysotoxum* and the leaf extract of *Grammatophyllum* sp. do not have a significant inhibiting effect on the expression of the Smac/DIABLO protein. The difference in concentration in the protein with the DMSO indicator is no more than −9% for the *Dendrobium chrysotoxum* root extract and −13% for the *Grammatophyllum* sp. leaf extract.

The extracts of the invention which can be obtained by extraction processes using polar solvents, were formulated as anti-ageing active agents in cosmetic compositions, and in particular for preventing or delaying the appearance of the signs of skin ageing or for slowing or attenuating the effects, or else also for promoting cell or tissue longevity.

Example 3: Anti-Ageing Cream for the Face

The extract of flowers of *Dendrobium chrysotoxum* used as an active agent in this cosmetic composition was obtained by reproducing the process of Example 1 (extract S-1).

The dry extract was dissolved at 2% w/w in a 60/40 v/v glycerol/water mixture.

This solution of extract was used as an active agent for the preparation of the cosmetic composition below (% expressed by weight relative to the final composition):

| Phase A | |
|---|---|
| 2% solution of *Dendrobium chrysotoxum* extract | 1 |
| Phenoxyethanol | 0.5 |
| Xanthan gum | 0.2 |
| Acrylates/C20-30 alkylacrylate crosspolymers | 0.2 |
| Tetrasodium EDTA | 0.1 |
| Water | qs | qs: quantity sufficient to dissolve the compounds of phase A.

| Phase B | |
|---|---|
| Hydrogenated polyisobutene | 4 |
| Squalane | 3 |
| Caprylic/capric triglycerides | 3 |
| Pentylene glycol | 3 |
| Glyceryl stearate | 3 |
| PEG-100 stearate | 2.5 |
| Beeswax | 1.5 |
| Dicaprylyl carbonate | 1.5 |
| Cetyl alcohol | 1 |
| Stearyl alcohol | 1 |
| Dimethicone | 1 |
| Phase C | |
| Sodium hydroxide | 0.04 |
| Water | qs 100 | qs 100: quantity sufficient for 100% of the final composition

The excipients of phase A were dispersed in water, then heated to 80° C., before dissolving all the other compounds including the water-glycol solution of *Dendrobium chrysotoxum* extract.

The compounds of phase B were heated to 85° C. to form a homogeneous phase.

Phase A was emulsified in phase B by means of an Ystral mixer.

Finally, the oil-in-water emulsion thus obtained was neutralized by means of a 0.04% w/w solution of sodium hydroxide (phase C), then cooled.

The composition obtained is an anti-ageing cream intended to be applied onto all or part of the face.

The invention claimed is:

1. A cosmetic treatment method for inhibition of the expression and/or the activity of the mitochondrial protein Smac/DIABLO in keratinocytes, and treatment of at least one skin condition selected from the group consisting of presence of wrinkles loss of lustre of skin complexion, loss of elasticity and/or suppleness of the skin, decrease in thickness of skin, and increase in skin dryness or roughness,
   said method comprising applying onto at least one part of the skin of the face or the body of a subject in need thereof, an effective amount of a composition comprising:
   i) at least one extract of flowers of an orchid *Dendrobium chrysotoxum* as an active agent that inhibits the expression and/or the activity of the mitochondrial protein Smac/DIABLO in keratinocytes, and consequently acts on said at least one skin condition,
   ii) and at least one cosmetically acceptable excipient that is selected from the group consisting of pigments, colorants, polymers, surfactants, rheological agents and perfumes,
   wherein the extract is obtained by a process comprising a step of placing the flowers in a solvent comprising at least 50% v/v of ethanol and up to 100% v/v of ethanol, the balance consisting of water, and
   wherein the composition contains from 0.0001% to 1% by weight of dry extract relative to the total weight of the composition.

2. The method of claim 1, wherein the extract is obtained by a process comprising a step of placing the flowers in a solvent comprising ethanol/water 90/10 v/v.

3. The method of claim 1, wherein the extract is obtained by a process comprising a step of placing the flowers in a solvent comprising 100% ethanol.

4. The method of claim 1, wherein the extract is obtained by a process comprising a step of placing the flowers in a solvent comprising ethanol/water 50/50 v/v.

5. The method of claim 1, wherein the extract is obtained by a process comprising a step of placing the flowers in a solvent comprising ethanol/water 70/30 v/v.

6. The method of claim 1, wherein the extract is obtained by a process comprising a step of placing the flowers in a solvent comprising at least 50% v/v of ethanol and up to 70% v/v of ethanol, the balance consisting of water, at ambient temperature.

7. The method of claim 1, wherein the extract is obtained by a process comprising a step of placing the flowers in a solvent at reflux or at ambient temperature.

8. The method of claim 1, wherein said composition comprises from 0.001% to 0.01% by weight of the dry extract relative to the total weight of the composition.

9. The method of claim according to claim 1, wherein said composition comprises a combination of the extract of flowers of the orchid *Dendrobium chrystoxum* with at least one other cosmetically acceptable active agent, in the form of purified substances and/or extracts.

10. The method of claim 9, wherein said composition further comprises one or more other active agents selected from the group consisting of forskolin, a plant extract from *Coleus forskolii*, a plant extract from *Nostoc commune*, a plant extract from *Butea frondosa*, a plant extract from *Neochloris oleabundans*, a plant extract from *Scenedesmus dimorphus*, a plant extract from *Curcuma longa*, a plant extract from *Crocus sativus*, a plant extract from *Daniellia oliveri*, a plant extract from *Lepechinia caulescens*, a plant extract from *Limnophila conferta*, and mixtures thereof.

11. The method of claim 9, wherein said composition comprises at least one extract of another part of the orchid *Dendrobium chrysotoxum* or of another orchid or a substance purified from such and extract.

* * * * *